United States Patent
Jordan

(10) Patent No.: US 6,669,623 B1
(45) Date of Patent: Dec. 30, 2003

(54) MEDICAL PREPARATION FOR TREATING ARTHROSIS, ARTHRITIS AND OTHER RHEUMATIC JOINT DISEASES

(75) Inventor: Andreas Jordan, Berlin (DE)

(73) Assignee: MagForce Applications GmbH (DE)

(*) Notice: Subject to any disclaimer, the term of this patent is extended or adjusted under 35 U.S.C. 154(b) by 0 days.

(21) Appl. No.: 10/048,037

(22) PCT Filed: Aug. 9, 2000

(86) PCT No.: PCT/DE00/02720

§ 371 (c)(1),
(2), (4) Date: Jan. 23, 2002

(87) PCT Pub. No.: WO01/13949

PCT Pub. Date: Mar. 1, 2001

(30) Foreign Application Priority Data

Aug. 19, 1999 (DE) .......................... 199 40 220

(51) Int. Cl.[7] .......................... A61N 2/00; A61K 39/44; A61M 36/14; A01N 25/00
(52) U.S. Cl. .................. 600/9; 514/825; 424/178.1; 424/1.33; 424/1.11
(58) Field of Search .......................... 600/110; 128/898; 424/9.3, 130.1, 450, 9.1, 9.2, 9.321, 9.34, 423, 178.1, 617, 641, 646, 1.11–1.33; 514/825; 623/915, 920; 250/584

(56) References Cited

U.S. PATENT DOCUMENTS

| | | | |
|---|---|---|---|
| 4,303,636 A | * 12/1981 | Gordon | ............... 424/1.29 |
| 4,590,922 A | * 5/1986 | Gordon | ................. 600/10 |
| 4,758,429 A | 7/1988 | Gordon | |
| 5,149,319 A | 9/1992 | Unger | |
| 5,655,546 A | * 8/1997 | Halpern | ............... 128/898 |
| 6,251,365 B1 | * 6/2001 | Bauerlein et al. | ............ 424/9.3 |

FOREIGN PATENT DOCUMENTS

| | | | | |
|---|---|---|---|---|
| DE | 19716732 | * | 9/1998 | ........... A61B/5/55 |
| DE | 19726282 | | 12/1998 | |

OTHER PUBLICATIONS

Grady E.D. et al, *Combination of internal radiation therapy and hyperthermia to treat liver cancer*, Southern Medical Journal (1983) pp. 1101–1105.
Database Biosis Online!, Biosciences Information Service, Philadelphia, PA, US; Musai, Akira, *Development of Anti-cancer–Agent–Releasing microcapsules for Chemotherapy Combined with Embolo–Hyperthermic Therapy*, Nippon Acta Radiologica (1995), vol. 55, No. 1, pp. 50–57.

* cited by examiner

Primary Examiner—Eric F. Winakur
Assistant Examiner—Nikita R Veniaminov
(74) Attorney, Agent, or Firm—Wood, Phillips, Katz, Clark & Mortimer

(57) ABSTRACT

A medical preparation for treating arthrosis, arthritis and other rheumatic joint diseases comprises a suspension consisting of one-shelled or multi-shelled nanoscalar particles composed of a core containing iron oxide and of an inner shell with groups capable of forming cationic groups or, optionally, of at least one outer shell with neutral and/or anionic groups. Radionuclides and substances, said substances being cytotoxically active when subjected to heat, are bound to the inner shell. The preparation that is injected into the joint cavity and subjected to an alternating electromagnetic field promises an excellent treatment outcome due to the high rate of phagocytosis and the trimodal combinatorial effect of thermotherapy, radiotherapy and chemotherapy.

9 Claims, No Drawings

MEDICAL PREPARATION FOR TREATING ARTHROSIS, ARTHRITIS AND OTHER RHEUMATIC JOINT DISEASES

CROSS REFERENCE TO RELATED APPLICATION(S)

Not applicable.

STATEMENT REGARDING FEDERALLY SPONSORED RESEARCH OR DEVELOPMENT

Not applicable.

REFERENCE TO A MICROFICHE APPENDIX

Not applicable.

BACKGROUND OF THE INVENTION

This invention relates to a medical preparation for treating arthrosis, arthritis and other rheumatic joint diseases comprising a suspension of coated magnetizable particles that generate heat in the diseased tissue by applying an alternating electromagnetic field.

Chronically painful defects of the skeletal and locomotor system resulting in permanent restricted movement such as arthritis, arthrosis and rheumatic diseases are first of all treated—in addition to physical forms of therapy—by a systemic pharmacotherapy using analgesics and non-steroidal antiphlogistics and cortisone which does not combat the causes of the disease and has undesirable side-effects.

Another known therapy called radiosynoviorthesis uses stabilized isotopes with a range of only a few millimeters to combat the pathogenic growth of the synovium. These are injected into the diseased joint to damage the synovial cells by radiation and thus control the inflammatory process.

However, the efficacy of radiosynoviorthesis requires the phagocytic activity of macrophages that are present in increased numbers in the synovial fluid due to the inflammation but tend to decline in numbers the older the patients are, thus limiting the successful application of radiosynoviorthesis.

In accordance with U.S. Pat. No. 4,758,429, a patient would be given an intravenous injection of colloidal suspensions consisting of ferromagnetic, paramagnetic, or diamagnetic particles of either $Fe_2O_3$ or FeOOH that are less than 1 micron in size and have coatings comprising dextran, metalloporphyrins as well as inorganic and organic metal compounds as substituents in the iron core. Application of an alternating electromagnetic field is to provide energy to the diseased area, however it remains unclear how the coated iron oxide particles are supposed to get to the diseased site. Colloidal suspensions on the basis of iron oxide particles coated as described are incapable of effectively containing the inflammatory processes of arthritis, arthrosis, and other rheumatic diseases. Nanoscalar particles with a ferrimagnetic, ferromagnetic, or superparamagnetic core containing iron oxide and comprising at least two shells that encompass said core were disclosed in DE 197 26 282 as part of a tumor therapy by hyperthermia. In this invention, the shell adjacent to said core comprises numerous positively charged functional groups that facilitate easy absorption of the coated iron core into the tumor cell, and the tumor tissue decomposes said shell slowly enough for said core to adhere to the cell's surface and subsequently be absorbed by the cell. The outer shells are made of species that protect the positively charged groups of the inner shell underneath to make said nanoscalar particles appear neutral or negatively charged at their outer side. The particles form a magnetic fluid and are injected at various spots into the tumor tissue and, due to their design, are thus well distributed within the tumor tissue and well incorporated into the interior of the tumor cells. Successful treatment by hyperthermia is enabled after applying an alternating electromagnetic field and the temperatures it produces due to the even distribution of the nanoscalar particles.

BRIEF SUMMARY OF THE INVENTION

These known nanoscalar particles are not designed for treating joint diseases and cannot guarantee success in their present form. It is therefore the problem of this invention to provide a means for local and systemic treatment of arthrosis, arthritis and other rheumatic joint diseases that guarantees effective pain killing and containment of the inflammatory process in the diseased joints based on the heat generated by the iron oxide particles in an alternating electromagnetic field.

This problem is solved according to the invention by a preparation comprising the characteristics described in claim 1. The subclaims and the subsequent description of an embodiment disclose other characteristics and advantageous improvements of the invention.

The invention is based on the concept of using a suspension of nanoscalar particles designed based on the description given in DE 197 26 282 for treating rheumatic joint diseases, said particles comprising, in a first embodiment, a core containing iron oxide, an inner shell that encompasses said core and comprises groups capable of forming cationic groups, and an outer shell made of species comprising neutral and/or anionic groups, and radionuclides and cytotoxic substances bound to said inner shell. These nanoscalar particles may also be one-shelled, i.e. consist just of the core and the inner shell, designed as described above.

It has been found that despite the fact that phagocytic activity in the synovial fluid decreases as the patients' age increases, intracellular adsorption of the particles according to the invention in macrophages is increased even in pathologically changed macrophage titers in the joint cavity, and that the inflammatory process is controlled as said particles adhere to actively proliferating cells of the synovia. Due to these effects and the heat generated when applying an alternating electromagnetic field, the radionuclides show increased efficacy as compared to radiosynoviorthesis. Last but not least, success of treatment is increased beyond the additive effect of each component due to binding substances that have a cytotoxic effect when exposed to heat to the particles, as this efficiently combines radiotherapy, thermotherapy, and chemotherapy.

BRIEF DESCRIPTION OF THE SEVERAL VIEWS OF THE DRAWINGS

Not applicable.

DETAILED DESCRIPTION OF THE INVENTION

According to an embodiment that utilizes the invention, a suspension of nanoscalar particles formed by an iron oxide core and two shells, with doxorubicin as a heat-sensitive cytotoxic material and beta emitting radionuclides bound to said particles, is directly injected into the joint cavity to be treated. Depending on phagocytic activity in the synovia, the suspension will stay there without generating heat for a period of time that is determined before the therapy begins. This period can be from 1 hour to 72 hours. In this period, the two-shelled nanoparticles according to the invention are absorbed by the synovial fluid and flow into the inflamed synovial membrane. The therapist then ascertains using magnetic resonance tomography whether the nanoparticles are really deposited in the synovial membrane, the adjacent lymph nodes, and in the healthy tissue. If required, an extravasation to adjacent areas may be performed but this should not be necessary due to the high rate of phagocytosis.

Subsequently, the area is exposed to an alternating electromagnetic field with an excitation frequency in the range from 1 kHz and 100 MHz. Its actual value depends on the location of the diseased joint. While hands and arms are treated at higher frequencies, 500 kHz will be sufficient for back pain, the lower joints and the thigh joints. The alternating electromagnetic field brings out the localized heat; at the same time, the radionuclide and the cytotoxic substances (here: doxorubicin) are activated, and success of treatment beyond the added effects of its components is achieved due to the trimodal combinatorial effect of therapies and the differential endocytosis and high rate of phagocytosis of the nano-particles. This means that the synovial membrane shows increased and sustained sclerosing with this treatment as compared to other medical preparations and methods of treating rheumatic diseases.

The heat that can be generated by the alternating electromagnetic field applied to the nanoparticles, or, in other words, the duration of applying the alternating electromagnetic field to obtain a specific equilibrium temperature is calculated in advance based on the iron oxide concentration that is typically in the range from 0.01 to 50 mg/ml of synovial fluid and power absorption that is typically in the range from 50 to 500 mW/mg of iron. Then the field strength is reduced to keep the temperature on a predefined level of, for example, 45° C. However, there is a considerable temperature drop from the synovial layer treated to adjacent cartilage and bone tissue so that the cartilage layer and the bone will not be damaged by this heat treatment. The temperature in the cartilage layer is slightly increased as compared to normal physiological conditions (38° C. to 40° C.). The resulting stimulation of osteoblasts improves the reconstitution of degeneratively modified bone borders and cartilage. Repeated applications of the alternating electromagnetic field not only counteract recurring inflammation after the decline of radioactivity but—at an equilibrium temperature in the range from 38 to 40° C.—are also used to stimulate osteoblast division. When applying static magnetic field gradients, the particles can be concentrated in the treated joint ('magnetic targeting').

We claim:

1. A medical preparation including nanoscalar particles that generate heat when an alternating electromagnetic field is applied, said nanoscalar particles comprising:
   a core containing iron oxide and an inner shell with groups that are capable of forming cationic groups, wherein the iron oxide concentration is in the range from 0.01 to 50 mg/ml of synovial fluid at a power absorption in the range from 50 to 500 mW/mg of iron and heating to a temperature in the range from 42 to 50° C.; and
   pharmacologically active species bound to said inner shell selected from the group consisting of thermosensitizers and thermosensitive chemotherapeutics or isotopes thereof;
   wherein said preparation is used for treating arthrosis, arthritis and rheumatic joint diseases by directly injecting said nanoscalar particles into the synovial fluid, said nanoscalar particles being absorbed by said fluid and transported to the inflamed synovial membrane where they are activated after a predefined period of time by applying said alternating electromagnetic field.

2. The medical preparation according to claim 1, characterized in that the temperature that can be achieved in the cartilage and bone layer adjacent to the synovial membrane by applying said alternating electro-magnetic field is between 38 and 40° C., which stimulates the osteoblasts.

3. A medical preparation including nanoscalar particles that generate heat when an alternating electromagnetic field is applied, said nanoscalar particles comprising:
   a core containing iron oxide and an inner shell with groups that are capable of forming cationic groups; and
   pharmacologically active radionuclides bound to said inner shell using chelating agents;
   wherein said preparation is adapted to be used for treating arthrosis, arthritis and rheumatic joint diseases by directly injecting said nanoscalar particles into the synovial fluid, said nanoscalar particles when injected being absorbed by said fluid and transported to the inflamed synovial membrane where they are activated after a predefined period of time by applying said alternating electromagnetic field.

4. The medical preparation according to claim 3, characterized in that said radionuclides are beta emitters of short range and with a half-life in the range from several hours to several days to protect the cartilage and bones.

5. The medical preparation according to claim 4, characterized in that said radioactive beta emitters preferably are Y-90, Rh-186, or Er-169.

6. The medical preparation according to claim 3, further comprising thermosensitive cytotoxic agents bound to said inner shell, wherein said agents are doxorubicin, epirubicin, or ifosfamide.

7. The medical preparation according to claim 3, characterized in that the excitation frequency of said alternating electromagnetic field for activating the injected preparation after a predefined period of time is in the range from 1 kHz to 100 MHz depending on the location of the preparation in the body.

8. The medical preparation according to claim 3, wherein the nanoscalar particles are adapted to be concentrated in specific locations by applying static magnetic field gradients when introduced into the joint.

9. The medical preparation of claim 3, further comprising at least one outer shell with at least one of neutral and anionic groups.

* * * * *